(12) United States Patent
Lesniak et al.

(10) Patent No.: US 10,532,014 B2
(45) Date of Patent: Jan. 14, 2020

(54) PRESERVATIVE SYSTEM BASED ON ORGANIC ACIDS

(71) Applicant: Colgate-Palmolive Company, New York, NY (US)

(72) Inventors: Ewelina Lesniak, Linden, NJ (US); Kathy Potechin, Short Hills, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/752,998

(22) PCT Filed: Aug. 18, 2015

(86) PCT No.: PCT/US2015/045623
§ 371 (c)(1),
(2) Date: Feb. 15, 2018

(87) PCT Pub. No.: WO2017/030560
PCT Pub. Date: Feb. 23, 2017

(65) Prior Publication Data
US 2018/0235858 A1  Aug. 23, 2018

(51) Int. Cl.
| A61K 8/365 | (2006.01) |
| A01N 37/36 | (2006.01) |
| A61K 8/368 | (2006.01) |
| A61Q 19/00 | (2006.01) |

(52) U.S. Cl.
CPC ............... *A61K 8/365* (2013.01); *A01N 37/36* (2013.01); *A61K 8/368* (2013.01); *A61Q 19/007* (2013.01); *A61K 2800/524* (2013.01); *A61K 2800/5922* (2013.01)

(58) Field of Classification Search
CPC ........ A01N 37/36; A01N 25/04; A01N 37/10; A61K 8/365; A61K 8/368; A61K 2800/52; A61K 2800/10; A61K 2800/5922; A61Q 19/007; A61Q 19/00
See application file for complete search history.

(56) References Cited

U.S. PATENT DOCUMENTS

| 4,941,995 | A | 7/1990 | Richards |
| 6,436,378 | B1 | 8/2002 | Mahashabde et al. |
| 9,555,018 | B2 | 1/2017 | Consalo et al. |
| 2003/0147825 | A1* | 8/2003 | Chiarelli ................. A61K 8/06 424/70.11 |
| 2009/0036543 | A1 | 2/2009 | Holzl et al. |
| 2013/0236561 | A1* | 9/2013 | Meyer .................... A61K 8/361 424/605 |

FOREIGN PATENT DOCUMENTS

| EP | 1964541 | 9/2008 |
| EP | 2182027 | 5/2010 |
| EP | 2181696 | 5/2013 |
| JP | 2006-306848 | 11/2006 |
| RU | 2380099 | 1/2009 |
| WO | 2013/028082 | 2/2013 |

OTHER PUBLICATIONS

Computer Translation oif EP 2181696 2015.*
Tom's of Maine, 2014 skin care moisturizing lotion provided by applicant on Form 1449, 2014.*
Tom's of Maine, 2014, "Moisturizing Lotion," Mintel GNPD AN: 2752949.
International Search Report and Written Opinion of the International Searching Authority in International Application No. PCT/US2015/045623, dated Oct. 20, 2015.

* cited by examiner

*Primary Examiner* — Blessing M Fubara

(57) ABSTRACT

Discloses a preservative system for personal care products comprising citric acid, lactic acid, benzoic acid and gluconic acid, and compositions and methods of preserving personal care compositions using said system.

11 Claims, No Drawings

PRESERVATIVE SYSTEM BASED ON ORGANIC ACIDS

BACKGROUND

Personal care products require preservatives to prevent the growth of microorganisms, especially bacteria, yeast and molds. While manufacturers may take stringent precautions to prevent microbial contamination during manufacture, it is inevitable that once a product has been newly opened by a consumer, there is a significant risk of contamination and subsequent microbial growth. Such microbial growth can result in the spoilage of the consumer product, compromising its performance. It is therefore customary to add preservative agents to personal care products at the time of manufacture. Oil-in water emulsions are known to be particularly susceptible to microbial growth.

The choice of preservative agents must be carefully considered into order to balance multiple concerns. Such concerns include cost, availability, toxicity, environmental risk, irritation, compatibility with other ingredients, and robustness against microbial growth. Many common preservative compounds can be irritating at high concentrations, yet ineffective at low concentrations. Other important factors relate to the nature of the personal care product, including its manner and frequency of use, expected shelf-life, and expected duration of use. In order to optimize properties, many personal care compositions employ a mixture of preservative agents, but this requires careful optimization of the amounts of each agent. Mixed preservative systems may be difficult to formulate, but provide the added benefit that the individual ingredients may be able to inhibit microbial growth of different organisms using different mechanisms of action, thus resulting in a broader spectrum of antimicrobial activity.

Traditional preservatives used in personal care products include para-hydroxybenzoic acid derivatives (parabens), aldehydes (e.g., formaldehyde, benzaldehyde), alkyl benzoates, benzoic acid salts (e.g., sodium benzoate), formic acid salts, arylphenols ortho phenylphenol), halogenated diphenyl ethers (e.g., triclosan), quaternary ammonium compounds (e.g., cetylpyridinium chloride, benzethonium chloride, benzalkonium chloride), nitrates and nitrites, and guanidine compounds (e.g., poly(hexamethylene biguanide)).

It has become particularly commercially desirable to formulate personal care products using ingredients that minimize risks to consumer's health and environmental impact. It has been difficult to develop effective preservative systems for personal care products which use as preservatives components with low health and environmental risks.

Consequently, there is a need for new, improved preservative systems for personal care products, which are inexpensive, robust, non-irritating and compatible with personal care formulations.

BRIEF SUMMARY

The inventors have developed an improved preservative system that does not require the inclusion of traditional anti-microbial agents, such as quaternary ammonium compounds, parabens, halogenated diphenyl ethers (e.g., triclosan), and phenoxyethanols. This preservative system can be effectively employed in a variety of personal care products, including cosmetics, lotions, cleansing products, and sun-bathing products. The preservative system presents a low risk to the health of consumers and to the environment.

In a first aspect, the present disclosure provides a preservative system comprising the organic acids citric acid, lactic acid, benzoic acid and gluconic acid, each in free or salt form. In some embodiments, the preservative system consists of, or consists essentially of, a mixture of citric acid, lactic acid, benzoic acid and gluconic acid, each in free or salt form. In some embodiments, one or more of the four acids is in free form. In some embodiments, each of the four acids is in free form.

In a second aspect, the present disclosure provides a personal care composition (e.g., a lotion, e.g., a moisturizing lotion), comprising an effective amount of a preservative system comprising citric acid, lactic acid, benzoic acid and gluconic acid. In some embodiments, the composition comprises a preservative system consisting of a mixture of citric acid, lactic acid, benzoic acid and gluconic acid.

In a third aspect, the present disclosure provides a method of preserving a personal care composition against microbial growth (e.g., bacterial or fungal, including yeast and mold), the method comprising the step of introducing into a personal care composition during manufacture a combination of citric acid, lactic acid, benzoic acid and gluconic acid. In some embodiments, the method does not include the addition of any other preservative agents.

DETAILED DESCRIPTION

Unless otherwise specified, all percentages and amounts expressed herein and elsewhere in the specification should be understood to refer to percentages by weight. Also, the term "about," when used in reference to a range of values, should be understood to refer to either value in the range, or to both values in the range. As used throughout, ranges are used as shorthand for describing each and every value that is within the range. Any value within the range can be selected as the terminus of the range.

As used herein, the terms "personal care composition" and "personal care product" includes creams, emulsions, lotions and gels for the skin (e.g., face, hands, feet, etc.), including cosmetic products and cosmetic-removal products, deodorant and antiperspirant products, hair care products, shaving products (e.g., creams, gels and foams), sun bathing products (e.g., sunscreen compositions and tanning compositions), insect repellent products, skin care products and personal cleansing products (e.g., liquid soaps, foams, gels, and lotions).

As used herein, "free form" of a carboxylic acid refers to a carboxylic acid in the state in which each carboxylic acid functional group is protonated (COOH). As used herein "salt form" refers to any form in which at least one carboxylic acid functional group is unprotonated, and therefore, in the form of a salt with a positively charged counterion (e.g., sodium, potassium, calcium, magnesium, lithium, ammonium, zinc, stannous, etc.). Salt forms include, for example, sodium benzoate, sodium gluconate, sodium lactate, monosodium citrate, disodium citrate and trisodium citrate.

Unless otherwise specified, any reference to "lactic acid", "citric acid", "gluconic acid" or "benzoic acid" herein throughout, refers to either the free form or any salt form of said acid.

In a first aspect, the present disclosure provides a preservative system (Preservative System I) for use in personal care compositions comprising citric acid, lactic acid, benzoic acid and gluconic acid. In some embodiments, the preservative system consists of citric acid, lactic acid, benzoic acid and gluconic acid. In some embodiments, the preservative system consists essentially of citric acid, lactic acid, benzoic acid and gluconic acid. In some embodiments, the preservative system does not include parabens, phenoxyethanol, halogenated diphenyl ethers (e.g., triclosan) or quaternary ammonium compounds.

In exemplary embodiments, the present disclosure provides the following exemplary preservative systems:

1.1 Preservative System I, wherein the system comprises lactic acid and benzoic acid in a 1:1 to ratio, e.g., a 1:1 to 4:1 ratio, a 2:1 to 4:1 ratio, a 2:1 to 3:1 ratio, or about a 2.5:1 ratio or about a 2.4:1 ratio.

1.2 Preservative System I or 1.1, wherein the system comprises gluconic acid and lactic acid in a 3:1 to 1:3 ratio, e.g., a 3:1 to 1:2 ratio, a 3:1 to 1:1 ratio, a to 1:1 ratio, or about a 1.5:1 ratio or about a 1.25:1 ratio.

1.3 Preservative System I, or any of 1.1-1.2, wherein the system comprises benzoic acid and citric acid in a 3:1 to 1:3 ratio, e.g., a 2:1 to 1:3 ratio, a 2:1 to 1:2 ratio, a 1:1 to 1:2 ratio, or about 1:1 ratio.

1.4 Preservative System I, or any of 1.1-1.3, wherein the system comprises benzoic acid and gluconic acid in a 1:1 to 1:6 ratio, e.g., a 1:2 to 1:6 ratio, a 1:2 to 1:5 ratio, a 1:2 to 1:4 ratio, or about a 1:3 ratio.

1.5 Preservative System I or any of 1.1-1.4, wherein the system comprises benzoic acid, lactic acid, citric acid and gluconic acid in about a 1:1:1:1 ratio, or about a 1:2:1:1 ratio, or about a 1:2:1:2 ratio, or about a 1:2:1:3 ratio, or about a 1:2:2:2 ratio, or about a 1:2:2:3 ratio, or about a 1:2:2:4 ratio, or about a 1:3:1:3 ratio, or about a 1:3:2:3 ratio, or about a 1:2.5:1:3 ratio, or about a 1:2.4:1:3 ratio.

1.6 Preservative System I or any of 1.1-1.5, wherein the system comprises benzoic acid, lactic acid, citric acid and gluconic acid in about a 1:2.4:1:3 ratio.

1.7 Preservative System I or any of 1.1-1.6, wherein one or more of the benzoic acid, lactic acid, citric acid or gluconic acid is present, in whole or in part, as a salt form.

1.8 Preservative System I or any of 1.1-1.7, wherein two or more, or three or more, or all four of the benzoic acid, lactic acid, citric acid or gluconic acid is present, in whole or in part, as a salt form.

1.9 Preservative System I or any of 1.1-1.6, wherein all four of the benzoic acid, lactic acid, citric acid and gluconic acid are present as their free forms.

1.10 Preservative System I or any of 1.1-1.9, wherein the preservative system does not contain any preservative agents other than benzoic acid, lactic acid, citric acid and gluconic acid.

1.11 Preservative System I or any of 1.1-10, which provides a micro-robustness index (MRI) of greater than or equal to 0.75, e.g., greater than or equal to 1.0.

1.12 Preservative System I or any of 1.1-1.11, which passes APET challenge (Antimicrobial Preservation Effectiveness Test), e.g., either aged or unaged APET, or both aged and unaged APET.

1.13 Preservative System I or any of 1.1-1.12, wherein the preservative system comprises benzoic acid, lactic acid, citric acid and gluconic acid, in a ratio other than about 1:2.4:1:3.

In a second aspect, the present disclosure provides a personal care composition (Composition 1), comprising an effective amount of a preservative system comprising citric acid, lactic acid, benzoic acid and gluconic acid. In some embodiments, the composition comprises a preservative system consisting of a mixture of citric acid, lactic acid, benzoic acid and gluconic acid. In some embodiments, the composition comprises a preservative system consisting essentially of a mixture of citric acid, lactic acid, benzoic acid and gluconic acid.

In exemplary embodiments, the present disclosure provides the following exemplary personal care compositions:

1.1 A personal care composition comprising Preservative System I or any of 1.1-1.13.

1.2 Composition 1 or 1.1, wherein the composition comprises benzoic acid at from 0.01 to 5% by weight of the composition, e.g., from 0.05% to 4%, or from 0.1% to 3%, or from 0.2% to 2%, or from 0.25% to 1.5%, or from 0.1% to 1%, or from 0.25% to 1%, or from 0.15% to 0.5%, or from 0.15% to 1%, or from 0.15% to 0.75%, or from 0.25% to 0.75%, or from 0.4% to 0.6%, or from 0.2% to 0.3%, or from 0.25 to 1.25%, or from 0.5% to 1%, or from 0.5% to 0.8%, or from 0.45% to 0.75%, or about 0.25%, or about 0.5%, or about 0.6%, or about 0.75%, or about 1%.

1.3 Composition 1 or any of 1.1-1.2, wherein the composition comprises lactic acid at from 0.01 to 5% by weight of the composition, e.g., from 0.05% to 4%, or from 0.1% to 3%, or from 0.2% to 2%, or from 0.25% to 1.5%, or from 0.1% to 1%, or from 0.25% to 1%, or from 0.15% to 0.5%, or from 0.15% to 1%, or from 0.15% to 0.75%, or from 0.25% to 0.75%, or from 0.4% to 0.6%, or from 0.2% to 0.3%, or from 0.25% to 1.25%, or from 0.5% to 1%, or from 0.5% to 0.8%, or from 0.45% to 0.75%, or about 0.25%, or about 0.5%, or about 0.6%, or about 0.75%, or about 1%.

1.4 Composition 1 or any of 1.1-1.3, wherein the composition comprises citric acid at from 0.01 to 5% by weight of the composition, e.g., from 0.05% to 4%, or from 0.1% to 3%, or from 0.2% to 2%, or from 0.25% to 1.5%, or from 0.1% to 1%, or from 0.25% to 1%, or from 0.15% to 0.5%, or from 0.15% to 1%, or from 0.15% to 0.75%, or from 0.25% to 0.75%, or from 0.4% to 0.6%, or from 0.2% to 0.3%, or from 0.25% to 1.25%, or from 0.5% to 1%, or from 0.5% to 0.8%, or from 0.45% to 0.75%, or about 0.25%, or about 0.5%, or about 0.6%, or about 0.75%, or about 1%.

1.5 Composition 1 or any of 1.1-1.4, wherein the composition comprises gluconic acid at from 0.01 to 5% by weight of the composition, e.g., from 0.05% to 4%, or from 0.1% to 3%, or from 0.2% to 2%, or from 0.25% to 1.5%, or from 0.1% to 1%, or from 0.25% to 1%, or from 0.15% to 0.5%, or from 0.15% to 1%, or from 0.15% to 0.75%, or from 0.25% to 0.75%, or from 0.4% to 0.6%, or from 0.2% to 0.3%, or from 0.25% to 1.25%, or from 0.5% to 1%, or from 0.5% to 0.8%, or from 0.45% to 0.75%, or about 0.25%, or about 0.5%, or about 0.6%, or about 0.75%, or about 1%.

1.6 Composition 1 or any of 1.1-1.5, wherein the composition comprises benzoic acid, lactic acid, citric acid and/or gluconic acid in the ratios as provided in any of Preservative Systems 1.1 to 1.6.

1.7 Composition 1 or any of 1.1-1.6, wherein the composition comprises 0.1% to 0.5% benzoic acid, 0.5% to 0.75% lactic acid, 0.1% to 0.5% citric acid, and 0.5% to 1% gluconic acid, each by weight of the composition.

1.8 Composition 1 or any of 1.1-1.7, wherein the composition comprises about 0.25% benzoic acid, about 0.60% lactic acid, about 0.25% citric acid, and about 0.75% gluconic acid, by weight of the composition.

1.9 Composition 1 or 1.1-1.8, which has a micro-robustness index (MRI) of greater than or equal to 0.75, e.g., greater than or equal to 1.0.

1.10 Composition 1 or 1.1-1.9, which passes APET challenge (Antimicrobial Preservation Effectiveness Test), e.g., either aged or unaged APET, or both aged and unaged APET.

1.11 Composition 1 or any of 1.1-1.10, wherein the composition further comprises one or more ingredients selected from among:
  (a) humectants (e.g., glycerin, sorbitol, propylene glycol),
  (b) fatty acids (e.g., caproic acid, caprylic acid, capric acid, lauric acid, myristic acid, palmitic acid, palmitoleic acid, stearic acid, oleic acid, linolenic acid, linoleic acid, arachidic acid, arachidonic acid),
  (c) fatty alcohols (e.g., cetearyl alcohol, cetyl alcohol, stearyl alcohol, oleyl alcohol),
  (d) esters of fatty acids (e.g., esters of caproic acid, caprylic acid, capric acid, lauric acid, myristic acid, palmitic acid, palmitoleic acid, stearic acid, oleic acid, linolenic acid, linoleic acid, arachidic acid, arachidonic acid, with alcohols such as glycerol, propylene glycol, sorbitan, isopropyl alcohol, caproic alcohol, capryl alcohol, capric alcohol, lauryl alcohol, myristyl alcohol, cetearyl alcohol, cetyl alcohol, palmoleyl alcohol, stearyl alcohol, oleyl alcohol, linoyl alcohol, linolenyl alcohol, arachidyl alcohol, arachidonyl alcohol) such as isopropyl myristate, capryl stearate, isopropyl olivate, cetearyl olivate, cetearyl oleate, glyceryl caprylate, glyceryl stearate citrate, and sorbitan olivate), natural and synthetic triglycerides (e.g., di- or tri-glycerides of fatty acids, such as glyceryl caprate or caprylic/capric triglyceride),
  (e) natural fats and oils (e.g. vegetable oil, coconut oil, sesame oil, avocado oil, corn oil, castor oil, shea butter, cocoa butter, soybean oil, sunflower oil, safflower oil, olive oil and tallow),
  (f) waxes (e.g., cetearyl wax, beeswax, carnauba wax, lanolin wax, candelilla wax, and paraffin wax),
  (g) Thickeners (e.g., silicas, xanthan gum, guar gum, agar, alginates, carrageenan, gellan gum, pectins, and modified cellulose polymers, such as hydroxycellulose, hydroxypropyl cellulose, hydroxyethyl cellulose, hydroxybutyl cellulose, hydropropyl methylcellulose, hydroxyethyl propyl cellulose),
  (h) Emulsifiers (e.g. polyethylene glycol esters, fatty alcohol polyglycol ethers, fatty acid polyglycol ethers, polyglycerol fatty acid esters, sorbitol, sorbitan, and mono- and di-fatty acid esters of sorbitan),
  (i) Sunscreen actives (e.g., titanium dioxide, zinc oxide, and UV absorption inhibitors, such as octyl methoxy cinnamate, benzophenone-3, and methylene bis-benzotriazolyl tetramethyl butyl phenol),
  (j) Vitamins (e.g., vitamin A, vitamin E, esters of vitamin A or vitamin E, such as vitamin E acetate and retinyl palmitate).
1.12 Composition 1 or any of 1.1-1.11, wherein the composition is oil-in-water emulsion.
1.13 Composition 1 or any of 1.1-1.12, wherein the composition is a cream, lotion or gel for the skin (e.g., face, hands, feet, etc.).
1.14 Composition 1 or any of 1.1-1.13, wherein the composition is a cosmetic product, cosmetic-removal product, deodorant or antiperspirant product, hair care product, shaving product (e.g., creams, gels and foams), sun bathing product (e.g., sunscreen compositions and tanning compositions), insect repellent product, skin care product or personal cleansing product (e.g., liquid soaps, foams, gels, and lotions).
1.15 Composition 1 or any of 1.1-1.14, further comprising natural biological extracts, such as essential oils or fragrances (e.g., Amyris oil, cedarwood oil, cocoa absolute, copaiba balsam, menthe oil pays, myrrh resin, patchouli oil, vanillin, vetiver oil, Aloe extract, lemon extract, orange extract, mandarin extract, and oil or extract of anise, clove, basil, aniseed, cinnamon, geranium, rose, mint, lavender, thyme, rosemary, citronella, cypress, eucalyptus, peppermint, and sandalwood).
1.16 Composition 1 or any of 1.1-1.15 further comprising water, e.g., from 5-90% water by weight of the composition, for example, 10%-80%, 15%-80%, 20%-80%, 25%-80%, 25%-75%, 30%-75%, 30%-80%, 40%-80%, 40%-70%, 50%-75%, 50%-70%, 50%-65%, or 60%-70%, or 65-70%, or about 65%, or about 66%, or about 67%, or about 68%.
1.17 Composition 1 or any of 1.1-1.15, wherein the pH of the composition is from 3-5, for example, from 3.5-4.5, or from 3.5-4.1, or from 3.7-4.1, or from 3.8-4.0, or about 3.9.
1.18 Composition 1 or any of 1.1-1.17, wherein the composition is free of parabens, phenoxyethanol, quaternary ammonium compounds, halogenated diphenyl ethers (e.g., triclosan), or any combination thereof.
1.19 Composition 1 or any of 1.1-1.18, wherein the preservatives present in the composition consists essentially of, or consists of, Preservative System I or any of 1.1-1.13.
1.20 Composition 1 or any of 1.1-1.19, wherein the composition comprises 0.1% to 0.4% benzoic acid, 0.35% to 0.75% lactic acid, 0.1% to 0.4% citric acid, and 0.6% to 0.9% gluconic acid, further wherein the composition does not comprise 0.25% benzoic acid, 0.60% lactic acid, 0.25% citric acid, and 0.75% gluconic acid, by weight of the composition.
1.21 Composition 1.20, herein the composition comprises benzoic acid, lactic acid, citric acid and gluconic acid, in a ratio other than about 1:2.4:1:3.

In a third aspect, the present disclosure provides a method (Method 1) of preserving a personal care composition against microbial growth (e.g., bacterial or fungal, including yeast and mold), the method comprising the step of introducing into a personal care composition during manufacture a combination of citric acid, lactic acid, benzoic acid and giuconic acid. In some embodiments, the method does not include the addition of any other preservative agents (e.g., parabens, phenoxyethanol, quaternary ammonium compounds, halogenated diphenyl ethers (e.g., triclosan), or any combination thereof).

In exemplary embodiments, the present disclosure provides the following exemplary methods:
1.1 Method 1.0, wherein the citric acid, lactic acid, benzoic acid and gluconic acid added to the personal care composition constitutes any of Preservative System I or 1.1-1.13.
1.2 Method 1 or 1.1, wherein the resulting composition is a personal care composition according to Composition 1 or any of 1.1-1.21.

The present disclosure also provides for the use of Preservative System I or any of 1.1-1.13 in the manufacture of a personal care composition, e.g., a personal care composition according to Composition 1 or any of 1.1-1.21. The present disclosure also provides for the use of Preservative System I, or any of 1.1-1.13, to preserve a personal care composition against microbial growth (e.g., bacterial or fungal, including yeast and mold). In some embodiments, the use of Preservative System I or any of 1.1-1.13 does not include the use of any other preservative agents (e.g. parabens, phenoxyethanol, quaternary ammonium compounds, halogenated diphenyl ethers (e.g., triclosan), or any combination thereof).

The compositions of the present disclosure, e.g., Composition 1 or any of 1.1-1.21, may be water-in-oil emulsions or oil-in-water emulsions, which typically comprise water, at least one water immiscible emollient component, and at least one emulsifying agent.

Illustrative examples of such emollient oils include mineral oils (e.g., paraffin oil, petroleum jelly oil), animal oils (e.g., fish oils and lanolin oil), vegetable oils (e.g., sweet almond oil, palm oil, avocado oil, olive oil, castor oil, cereal germ oil, canola oil, sunflower oil, soybean oil, and jojoba oil), triglycerides (e.g., caprylic/capric triglyceride), silicone oils (e.g., cyclomethicone), ester oils (e.g., butyl myristate, isopropyl myristate, cetyl myristate, isopropyl palmitate, isopropyl stearate, octyl stearate, isocearyl stearate), organic fatty alcohols (e.g., oleic alcohol, linolenic alcohol, linoleic alcohol, isostearyl alcohol, octyl dodecanol), and free fatty acids (e.g., linoleic acid, myristic acid, palmitic acid, stearic acid).

Illustrative examples of emulsifying agents include ethoxylated carboxylic acids, ethoxylated glycerides, glycol esters, monoglycerides, polyglyceryl esters, polyhydric alcohol esters and ethers, sorbitan/sorbitol esters, triesters of phosphoric acid, and ethoxylated fatty alcohols. Examples include glyceryl stearate, PEG-100 stearate, sorbitan stearate, PEG-40 stearate, polysorbate-20, polysorbate-60, polysorbate-80, and glyceryl oleate.

In some embodiments, personal care compositions of the present disclosure further comprise one or more ingredients selected from surfactants (including anionic surfactants, zwitterionic surfactants, cationic surfactants and nonionic surfactants, or mixtures thereof), coloring agents, fragrances, moisturizing agents, and amino acids.

Anionic surfactants useful herein include the water-soluble salts of alkyl sulfates and alkyl ether sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed.

Nonionic surfactants that can be used in the compositions can broadly be defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEEN®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl (C8-10) glucoside, coca (C8-16) glucoside, and lautyl (C12-16) glucoside), long chain tertiary amine oxides, long chain tertiary phosphine oxides, long chain diallyl sulfoxides, and mixtures of such materials.

Amphoteric surfactants that can be used can be broadly described as derivatives of aliphatic secondary and tertiary amines in which the aliphatic radical can be a straight chain or branched and wherein one of the aliphatic substituents contains from 8 to 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al. in U.S. Pat. No. 4,051,234.

Compositions and personal care products according to the present disclosure can be prepared by methods known to those skilled in the art. For example, in a typical preparative method, benzoic acid and aloe vera flakes are added to water heated to 60° C. and mixed for 15 minutes. A 5% solution (w/v) of rice powder in water is then prepared and heated to 80° C. After mixing for 30 minutes at 80° C., the rice powder solution is added to the benzoic acid/aloe vera solution and the whole is mixed for 15 minutes at 75-80° C. A mixture of glycerin and xanthan gum is then added, and the whole is maintained at 75-80° C. The remaining major oil-phase ingredients are combined and heated to 75-80° C. in a separate container (e.g., shea butter, vegetable oils, cetyl alcohol, fatty acids and esters), and then the separate oil and water phases are combined and mixed until smooth. Sodium hydroxide is added, followed by the desired complement of water. After cooling to 50-55° C., citric acid, lactic acid and gluconic acid are added, and the mixture is mixed and cooled to 40° C., at which temperature fragrance and vitamin E are added. Upon cooling 25-28° C., the fully homogenized mixture can be dispensed for packaging.

EXAMPLES

Exemplary embodiments of the present disclosure will be illustrated by reference to the following examples, which are included to exemplify, but not to limit the scope of the present invention.

In the examples and elsewhere in the description of the invention, chemical symbols and terminology have their usual and customary meanings. Temperatures are in degrees Celsius unless otherwise indicated. The amounts of the components are in weight percents based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., 7$^{th}$ ed. 1997).

Example 1: MRT and APET Analysis of Commercial Products

A selection of commercial lotion formulas were analyzed for their micro-robustness using two assays. The MRT (micro-robustness test) measures the ability of a formulation to resist the growth of bacteria, while the APET (antimicrobial preservation effectiveness test) measures the ability of a formulation to resist the growth of yeast, mold and bacteria.

The MRT is a challenge test assessing the antimicrobial efficacy of a compound or composition against a pool of microorganisms including *Burkholderia cepacia, Enterobacter cloacae, Escherichia coli, Klebsiella oxytoca, Klebsiella pneumoniae, Serratia marcescens, Providencia rettgeri, Pseudomonas aeruginosa, Pseudomonas putida, Staphylococcus aureus*, and *Staphylococcus saprophyticus*. Samples are challenged three times at 30 minute intervals with an inoculum of $10^7$ bacteria from the above listed pool. After 4, 6 and 24 hours, aliquots are tested to measure the log reduction of bacteria. Using these data, the area under the curve (AUC) is calculated and then converted into the Micro-Robustness Index (MRI) score. The higher the MRI, the greater the micro-robustness of the tested composition. The MRI is used as a quantitative measure of a composition's ability to withstand microbial challenge. An MRI score of equal to or greater than 0.75 is considered acceptable, while a score greater than 1.0 is preferred.

The APET test is a familiar test used in the cosmetic and personal care industry. The APET test is conducted under either aged or unaged conditions. Aged means that the product being tested has been maintained at a temperature of 40° C. and 75% relative humidity for 8 weeks, whereas the unaged test is performed on fresh product after manufacture and packaging. The test measures the growth of an inoculum of bacteria or mold in the presence of the tested composition. APET results in either a pass or fail rating. A passing APET test requires a greater than 99.9% reduction in the level of bacteria in the inoculum and a greater than 90.0% reduction in the level of mold in the inoculum.

The results shown in Table 1 below clearly show that many common personal care products on the market do not adequately protect the consumer from the risk of product spoilage and deterioration resulting from bacterial and/or fungal contamination. There is an urgent need for improved preservative systems for these kinds of products.

TABLE 1

| Sample Description (Preservative System Ingredients) | MRI | APET |
|---|---|---|
| Ultimate Care Body Lotion with Baobab Oil (phenoxyethanol, potassium sorbate, sodium benzoate) | 0.01 | Fail |
| Radiance Body Lotion with Royal Jelly and Natural Mica (sodium benzoate, phenoxyethanol) | 0.04 | Fail |
| Soothing Hypoallergenic Body Lotion (phenoxyethanol) | 0.66 | Fail |
| Age Refresh Rejuvenating Body Lotion (sodium benzoate, phenethyl alcohol) | 1.32 | Pass |
| Nourishing Daily Moisture Body Lotion (behenyl alcohol, phenoxyethanol) | 0.52 | Fail |
| Orange Petalooza Body Lotion (potassium sorbate) | 1.33 | Fail |
| Rich Replenishing Cocoa-Capuco Butter Lotion (lactic acid, sodium benzoate, phenoxyethanol) | 0.45 | Pass |
| Naturally Nourishing Milk & Honey Lotion (lactic acid, citric acid, sodium benzoate, phenoxyethanol, benzyl alcohol, benzyl benzoate) | 0.29 | Fail |
| Soothing Sensitive Aloe & Buttermilk Lotion (lactic acid, citric acid, sodium benzoate, phenoxyethanol, lactoperoxidase) | 0.34 | Fail |
| Daily Moisturizing Fragrance Free Lotion (benzyl alcohol) | 0.40 | Fail |

Example 2: Comparison of Acidic Preservative Systems

Applicants further used the MRT and APET tests to determine the micro-robustness of a daily moisturizing lotion preserved using various combinations of benzoic acid, lactic acid, citric acid and gluconic acid. The results clearly demonstrate the superiority of the four-acid preservative system. It should be noted that while Preservative System D showed passing test results, the formulation had unacceptably high viscosity. Additionally, while both formulations B and C passed the aged APET test, both showed some mold growth. In contrast, formulation E showed no mold growth during the test.

TABLE 2

| Preservative System | MRI | Unaged APEX | Aged APET | Comments |
|---|---|---|---|---|
| A. 0.25% benzoic acid, 0.60% lactic acid | 0.19 | Fail | Fail | Does not meet MRT/APET criteria |
| B. 0.35% benzoic acid, 0.68% lactic acid | 1.23 | Fail | Pass | Some yeast/mold growth observed* |
| C. 0.25% benzoic acid, 0.60% lactic acid, 0.50% citric acid | 0.96 | Pass | Pass | Some mold growth observed* |
| D. 0.25% benzoic acid, 0.60% lactic acid, 1.50% gluconic acid | 1.02 | Pass | Pass | Increase in viscosity |
| E. 0.25% benzoic acid, 0.60% lactic acid, 0.25% citric acid, 0.75% giuconic acid | 0.96 | Pass | Pass | No impact on viscosity; meets MRT and APET criteria |

*observed growth is in acceptable range

Example 3: Exemplary Compositions

Below are shown exemplary compositions prepared using the four-acid preservative system of the present disclosure.

|  | Daily Moisturizing Lotion | Hand Cream |
|---|---|---|
| Demineralized water and minors (fragrance, vitamins, etc.) | QS | QS |
| Glycerin (98-101%) | 5 | 5 |
| Coconut oil | 4.4 | 4.4 |
| Symbiomuls GC (blend of glyceryl stearate citrate, cetearyl alcohol and glyceryl caprylate | 4 | 4 |
| Shea Butter | 4 | 4.5 |
| Caprylic/Capric Triglyceride | 3.2 | 3.2 |
| Cetearyl Olivate/Sorbitan Olivate | 3 | 3 |
| Stearic Acid/Palmitic Acid | 3.00 | 3.00 |
| Cetyl Alcohol | 1.7 | 1.7 |
| Lactic Acid, 80% | 0.75 | 0.75 |
| Xanthan Gum | 0.32 | 0.5 |
| Sodium Hydroxide | 0.29 | 0.29 |
| Benzoic Acid | 0.25 | 0.25 |
| Rice Powder | 0.15 | 0 |
| Gluconic Acid, 50% | 1.5 | 1.5 |
| Citric Acid, 50% solution | 0.5 | 0.5 |

What is claimed is:

1. A preservative system for use in personal care compositions comprising citric acid, lactic acid, benzoic acid and gluconic acid, wherein the benzoic acid, lactic acid, citric acid and gluconic acid are in a 1:1:1:1 weight ratio, a 1:2:1:1 weight ratio, a 1:2:1:2 weight ratio, a 1:2:1:3 weight ratio, a 1:2:2:2 weight ratio, a 1:2:2:3 weight ratio, a 1:2:2:4 weight ratio, a 1:3:1:3 weight ratio, a 1:3:2:3 10 weight ratio, a 1:2.5:1:3 weight ratio, or a 1:2.4:1:3 weight ratio.

2. The preservative system of claim 1, wherein the benzoic acid, lactic acid, citric acid and gluconic acid are in about a 1:2.4:1:3 weight ratio.

3. The preservative system of claim 1, wherein one or more of the benzoic acid, lactic acid, citric acid or gluconic acid is present, in whole or in part, as a salt form.

4. The preservative system of claim 1, wherein all four of the benzoic acid, lactic acid, citric acid and gluconic acid are present as their free forms.

5. The preservative system of claim 1, wherein the preservative system does not contain any preservative agents other than benzoic acid, lactic acid, citric acid and gluconic acid.

6. A method of preserving a personal care composition against microbial growth, the method comprising the step of introducing the preservative system of claim 1 into a personal care composition.

7. A personal care composition comprising an effective amount of a preservative system, wherein the preservative system comprises citric acid, lactic acid, benzoic acid and gluconic acid, and wherein the composition comprises 0.1% to 0.5% benzoic acid, 0.5% to 0.75% lactic acid, 0.1% to 0.5% citric acid, and 0.5% to 1% gluconic acid, each by weight of the composition.

8. The personal care composition according to claim 7, wherein the composition comprises about 0.25% benzoic acid, about 0.60% lactic acid, about 0.25% citric acid, and about 0.75% gluconic acid, by weight of the composition.

9. The personal care composition according to claim 7, wherein the composition is a cosmetic product, cosmetic-removal product, deodorant or antiperspirant product, hair care product, shaving product, sun bathing product, insect repellent product, skin care product or personal cleansing product.

10. The personal care composition according to claim 9, which is a skin lotion.

11. The personal care composition according to claim 7, wherein the composition is free of parabens, phenoxyethanol, quaternary ammonium compounds, halogenated diphenyl ethers, or any combination thereof.

* * * * *

UNITED STATES PATENT AND TRADEMARK OFFICE
CERTIFICATE OF CORRECTION

PATENT NO. : 10,532,014 B2
APPLICATION NO. : 15/752998
DATED : January 14, 2020
INVENTOR(S) : Ewelina Lesniak et al.

Page 1 of 1

It is certified that error appears in the above-identified patent and that said Letters Patent is hereby corrected as shown below:

In the Specification

In Column 3, Line 8, after "in a 1:1 to", insert -- 5:1 --.

In Column 3, Line 13, after "1:1 ratio, a", insert -- 2:1 --.

In Column 4, Line 12, after "0.25", insert -- % --.

In Column 6, Line 30, delete "herein" and insert -- wherein --, therefor.

In Column 6, Line 39, delete "giuconic" and insert -- gluconic --, therefor.

In Column 7, Line 61, delete "lautyl" and insert -- lauryl --, therefor.

In Column 7, Line 63, delete "diallyl" and insert -- dialkyl --, therefor.

Signed and Sealed this
Thirty-first Day of March, 2020

Andrei Iancu
*Director of the United States Patent and Trademark Office*